(12) United States Patent
Chan et al.

(10) Patent No.: US 7,612,239 B2
(45) Date of Patent: Nov. 3, 2009

(54) METHOD FOR ASYMMETRIC ALKYNYLATION OF ALPHA-IMINO ESTERS

(75) Inventors: Albert S Chan, Hung Hom (HK); Jian-Xin Ji, Nashville, TN (US); Jing Wu, Hangzhou Zhejiang (CN)

(73) Assignee: The Hong Kong Polytechnic University, Hong Kong (CN)

( * ) Notice: Subject to any disclaimer, the term of this patent is extended or adjusted under 35 U.S.C. 154(b) by 157 days.

(21) Appl. No.: 11/913,773

(22) PCT Filed: May 17, 2006

(86) PCT No.: PCT/US2006/019141

§ 371 (c)(1), (2), (4) Date: Nov. 7, 2007

(87) PCT Pub. No.: WO2006/125030

PCT Pub. Date: Nov. 23, 2006

(65) Prior Publication Data

US 2008/0183010 A1      Jul. 31, 2008

Related U.S. Application Data

(60) Provisional application No. 60/682,647, filed on May 19, 2005.

(51) Int. Cl.
*C07C 209/60* (2006.01)
(52) U.S. Cl. .............. 564/468; 564/305; 564/393; 564/487
(58) Field of Classification Search ............ 564/468, 564/393, 305, 487
See application file for complete search history.

(56) References Cited

OTHER PUBLICATIONS

Greenspan et al., "Identification of dipeptidyl nitriles as potent and selective inhibitors of cathepsin B through structure-based drug design" J. Med. Chem., vol. 44, No. 26, pp. 4524-4534 (2001).
Ji et al., "Efficient synthesis of beta, gamma-alkynyl alpha-amino acid derivative by Ag(I)-catalyzed alkynylation of alpha-imino esters" Adv. Synth. Catal., vol. 346, pp. 42-44 (2004).
Ji et al., Catalytic asymmetric alkynylation of alpha-imino ester; A versatile approach to optically active unnatural alpha-amino acid derivatives, Proceedings of the National Academy of Sciences of the United States of America, vol. 102, No. 32 (2005).
Taggi et al., "Alpha-imino esters: Versatile substrates for the catalytic, asymmetric synthesis of alpha- and beta-amino acids and beta-lactams", Acc. Chem., vol. 36, pp. 11-14 (2003).

*Primary Examiner*—Elvis O Price
(74) *Attorney, Agent, or Firm*—Sandra S. Shim; John W. Kung

(57) ABSTRACT

Method for the preparation of asymmetric alkynylated α-amino esters of the formula

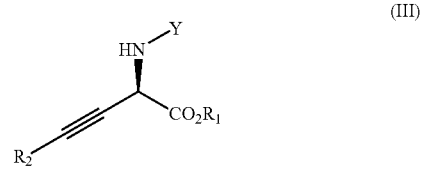

(III)

wherein $R_1$ and $R_2$ are independently optionally substituted alkyl cycloalkyl, aryl or heteroaryl, and Y is hydrogen or a nitrogen protecting group.

9 Claims, No Drawings

METHOD FOR ASYMMETRIC ALKYNYLATION OF ALPHA-IMINO ESTERS

This application claims benefit of U.S. Provisional Application No. 60/682,647, filed May 19, 2005.

FIELD OF THE INVENTION

The present invention relates to a method is the addition of a terminal alkyne to an α-imino ester.

BACKGROUND OF THE INVENTION

Enantiomeric α-amino acids, in particular, nonproteinogenic amino acids are of exceptional and rapidly increasing popularity as important tools in protein engineering and peptide-based drug discovery. Intense research has been focused on the preparation of enantiomerically enriched unnatural α-amino acids. Several approaches, for example, bioresolution routes as well as the rhodium-catalyzed asymmetric hydrogenation of enamides have shown good promise. However, there is still a need for an efficient and technically feasible method for the convenient synthesis of different types of unnatural amino acids derivatives.

An attractive strategy to accomplish such syntheses is the enantioselective nucleophilic addition to α-imino esters. This can be useful because a new chiral center and a new carbon-carbon bond can be established in a single operation and an appropriately designed side chain can be introduced as well. Prior work in the field mainly focused on the catalytic asymmetric alkylation of α-imino ester. Nucleophiles that have been used include enol silane, allyl-metal compounds, TMS-nitronate, ketones and nitroalkanes.

Recently, the alkynylation of α-imino esters by directly adding terminal alkynes to an α-imino ester in the presence of Ag(I) salts under mild reaction conditions has been reported. See, Ji et al., "Efficient Synthesis of β,γ-alkynyl α-amino acid derivatives by Ag(I) catalyzed alkynylation of α-imino esters", 346 ADV. SYNTH. CATAL. 42-44 (2004). However, this reported Ag(I)-catalyzed reaction, is not enantioselective even when a chiral ligand is employed, for example, aminophsophanes, diphosphanes and pybox.

Thus, there is need for a process to provide for the asymmetric terminal alkynylation of α-amino esters that can be used to synthesize optically active unnatural α-amino acids. The present invention addresses this need.

SUMMARY OF THE INVENTION

The present invention relates to a method for preparing asymmetric alkynylated α-amino esters of the formula

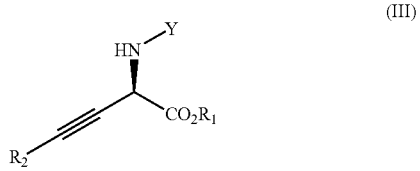

(III)

wherein $R_1$ and $R_2$ are independently optionally substituted alkyl, cycloalkyl, aryl or heteroaryl, and Y is hydrogen or a nitrogen protecting group; which method comprises reacting an α-imino ester of formula

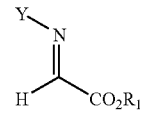

(I)

wherein $R_1$ and Y have meanings as defined for formula III with a terminal alkyne of formula

(II)

wherein $R_2$ has meaning as defined for formula III.

DETAILED DESCRIPTION OF THE INVENTION

The present invention relates to a method for the catalytic asymmetric alkynylation of α-imino esters.

As used herein, the term "α-imino ester" refers to a compound having the formula (I)

(Compound I)

wherein $R_1$ is optionally substituted alkyl, cycloalkyl, aryl or heteroaryl; and Y is hydrogen or a nitrogen protecting group.

As used herein, the term "optionally substituted alkyl" refers to unsubstituted or substituted straight- or branched-chain hydrocarbon groups having one to twenty carbon atoms, e.g., one to seven carbon atoms. Examples of unsubstituted alkyl groups, include, but are not limited to, methyl, ethyl, propyl, isopropyl ($^i$pr), n-butyl, t-butyl, isobutyl, pentyl, neopentyl, hexyl, isohexyl, heptyl, octyl and the like. Substituted alkyl groups include, but are not limited to, alkyl groups substituted by one or more of the following groups: hydroxyl, alkylamino, dialkylamino, cycloalkyl, alkenyl or alkoxy.

As used herein, the term "lower alkyl" refers to those optionally substituted alkyl groups as described above having one to six carbon atoms.

As used herein, the term "alkenyl" refers to any one of the above alkyl groups having at least two carbon atoms and further containing a carbon to carbon double bond at the point of attachment. Useful are groups having two to four carbon atoms.

As used herein, the terms "halogen", "halide" or "halo" refer to fluorine, chlorine, bromine and iodine.

As used herein, the term "alkoxy" refers to alkyl-O—.

As used herein, the term "cycloalkyl" refers to optionally substituted monocyclic aliphatic hydrocarbon groups of three to six carbon atoms, which may be substituted by one or more substitutents, such as alkyl or alkoxy.

Examples of monocylic hydrocarbon groups include, but are not limited to, cyclopropyl, cyclobutyl, cyclopentyl, cyclohexyl and the like.

As used herein, the term "aryl" refers to monocylic or bicyclic aromatic hydrocarbon groups having six to twelve carbon atoms in the ring portion, such as phenyl, biphenyl, naphthyl and tetrahydronaphthyl, each of which may optionally be substituted by one to four substituents, such as optionally substituted alkyl, cycloalkyl or alkoxy.

As used herein, the term "monocyclic aryl" refers to optionally substituted phenyl as described under aryl.

As used herein, the term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like; optionally substituted by, e.g., lower alkyl or lower alkoxy.

As used herein, the term "nitrogen protecting group" refers to substituents that can be introduced to protect nitrogen from undesired reactions with reaction components under the conditions used for carrying out a particular chemical transformation of the present invention. The need and choice of protecting groups for a particular reaction is known to one skilled in the art and depends on the structure and stability of the molecule of which the substituent is a part and the reaction conditions.

Well-known protecting groups that meet these conditions and their introduction and removal are described, e.g., in McOmie, *Protective Groups in Organic Chemistry*, Plenum Press, London, N.Y. (1973); and Greene and Wuts, *Protective Groups in Organic Synthesis*,John Wiley and Sons, Inc., NY (1999).

Examples of suitable nitrogen protecting groups for Y include, but are not limited to: p-methoxyphenyl ("PMP"), benzyl, methyl, and triphenylmethyl. Particularly useful are PMP and benzyl.

As used herein, the term "terminal alkyne" refers to a compound having the formula (II)

(Compound II)

wherein $R_2$ is optionally substituted alkyl, cycloalkyl, aryl or heteroaryl.

As used herein, the term "asymmetric alkynylated α-imino ester refers to a compound having the formula (III):

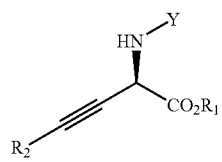
(Compound III)

wherein Y, $R_1$ and $R_2$ are as defined above.

Catalysts useful in the present invention comprise chiral ligands bound to a transition metal source, e.g., a transition metal, a transition metal salt or a transition metal complex. Such catalysts can be generated in situ or isolated prior to use.

Suitable transition metals for the catalyst system include, but are not limited to copper (Cu), iridium (Ir), nickel (Ni), palladium (Pd), platinum (Pt), rhodium (Rh) and ruthenium (Ru) and salts and complexes thereof. Particularly useful, e.g., is copper and complexes thereof. Further examples of such transition metal sources can be found, e.g., in Seyden-Penne, *Chiral Auxiliaries and Ligands in Asymmetric Synthesis*, John Wiley & Sons, Inc., NY (1995), which is hereby incorporated by reference.

Examples of transition metal complexes include, but are not limited to, IrCl.2COD, $Zn(OTf)_2$, $ZnCl_2$, $Sc(OTf)_3$, $CuO_2$, CuOAc, CuCl, CuI, $CuBF_4$, CuBr, $CuPF_5.4MeCN$, $CuOTf.0.5C_6H_6$, and $Cu(OTf)_2$. However, particularly useful as transition metal sources, are $CuPF_5.4MeCN$ and $CuOTf.0.5C_6H_6$.

Examples of chiral ligands include, but are not limited to, the following chiral ligands designated as 4, 5, 6, 7, 8a, 8b and 9 and enantiomers thereof, and enantiomeric mixtures thereof. However, particularly useful, are chiral ligands: 5, 7, 8a and 9, and enantiomers thereof and enantiomeric mixtures thereof. Chiral ligand 4 is 2,2'-bis (diphenylphosphino)-1,1'-binaphthyl (or, "Binap"). Chiral ligand 6 is 1-(2-Diphenylphosphino-1 -naphthyl)isoquinoline (or, "Quinap"). Chiral ligand 9 is bis(oxazolidine)-pyridine (or, "Pybox").

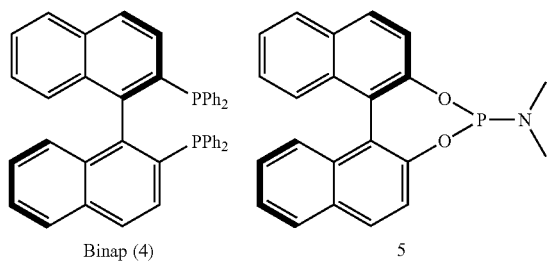

Binap (4)                    5

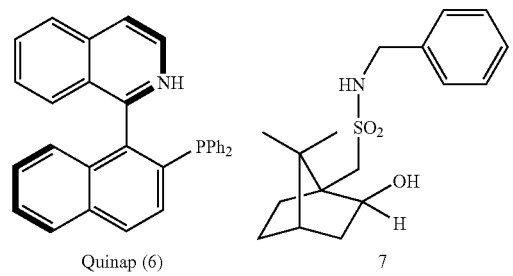

Quinap (6)                    7

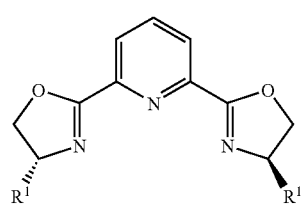

Pybox (8a): $R^1 = {}^iPr$
Pybox (8b): $R^1 = Ph$

-continued

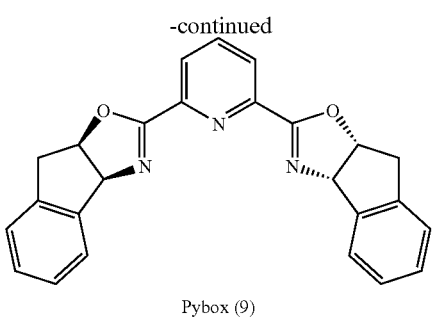

Pybox (9)

Examples of amine bases include, but are not limited to, PMP—H$_2$, Et$_3$N, $^i$Pr$_2$NH, Pr$_2$EtN, Cy$_2$NMe. However, particularly useful is PMP—H$_2$.

Each of the alkynylation reactions of Compound I (discussed below) is conducted in accordance with the following general procedure:

All reactions are conducted under a nitrogen atmosphere. All chemicals and solvents, e.g., organic solvents, are used as received without further purification unless otherwise stated. CH$_2$Cl$_2$, an organic solvent, is distilled from CaH$_2$. Compound I is synthesized according to methods known to one of ordinary skill in the art. See, e.g., Andrew Taggi et al., "A-imino esters: versatile substrates for the catalytic, asymmetric synthesis of α- and β-amino acids and β-lactams," 36 ACC. CHEM. RES. 10 -19 (2003).

Pybox (the chiral ligand 9) (9.7 mg, 0.025 mmol) and CuOTf.0.5C$_6$H$_6$ (6.5 mg, 0.025 mmol) are added to a dried 10-mL round-bottom flask containing a magnetic stirring bar. CH$_2$Cl$_2$ (1.0 mL) is added, and the mixture is stirred at room temperature for one hour. Other organic solvents that can also be used in the present invention are diethyl ether, tetrahydrofurane and dioxane. The solution is cooled to a temperature of about −10° C. The reaction temperature can range from about −40° C. to about 30° C.; e.g., from about −20° C. to 0° C. The α-imino ester (Compound I) (52.3 mg, 0.25 mmol) in CH$_2$Cl$_2$ (400 μL), the terminal alkyne (Compound II) (0.25 mmol) and PMP—NH$_2$ (an amine base)(3.2 mg, 025 mmol) in CH$_2$Cl$_2$ (100 μL) are sequentially added under vigorous stirring. The resulting solution was stirred at −10° C. and the reaction was monitored by TLC. Upon completion of the reaction, the mixture is filtered through a 1 cm×1 cm plug of silica gel which is subsequently washed with EtOAc (10 mL). The solution is poured into a separatory funnel and mixed well with EtOAc (25 mL) and H$_2$O (5 mL). The aqueous layer is discarded, and the organic layer is washed with saturated brine (5 mL). The resulting organic layer is dried over anhydrous Na$_2$SO$_4$, filtered, and then concentrated in vacuo. The purification of the residue by flash column chromatography (9:1 hexane-EtOAc as eluents) yields the desired alkynylation products as a light yellow oil.

For analysis, $^1$H NMR and $^{13}$C NMR spectra are recorded in CDCl$_3$ on a Varian AS 500 (500 and 125 MHz respectively) spectrometer at room temperature. Chemical shifts (δ) are expressed in ppm and J values are given in Hz. HRMS are carried out with ESI method on a Fisons VG platform or a Finnigan Model MAT-95 spectrometer. HPLC analyses are performed using a Waters Model 600 with a Waters 486 UV detector. Optical rotations are measured on a Perkin-Elmer Model 341 polarimeter in a 10 cm cell. Flash column chromatography was performed on silica gel (230-400 mesh).

EXAMPLE 1

Identification of Appropriate Transition Metals for Catalyst

TABLE 1

4-phenyl-1-butyne addition to α-imino ester catalyzed by different metal salts

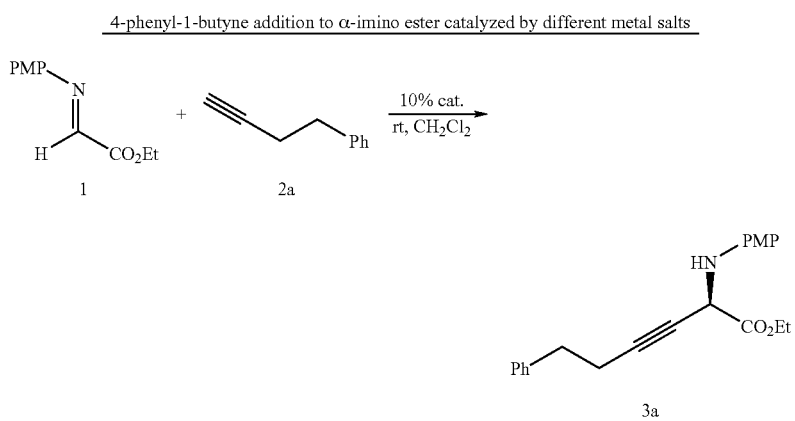

| Entry | Catalyst | Yield* (%) |
|---|---|---|
| 1 | IrCl•2COD, Zn(OTf)$_2$, ZnCl$_2$, Sc(OTf)$_3$, CuO$_2$, CuOAc | 0 |
| 2 | CuCl, CuBr | <10 |
| 3 | CuPF$_6$•4MeCN | 72 |
| 4 | CuOTf•0.5C$_6$H$_6$ | 70 |
| 5 | Cu(OTf)$_2$ | 35 |

Condition:
1 (0.5 mmol) and
2a (1.0 mmol) in CH$_2$Cl$_2$ (5 mL).
*Isolated yields.

A number of transition metals such as Zn(II), Cu(I)/(II), Ir(I) and Sc(III) as listed in Table 1, supra, are investigated. The addition of 4-phenyl-1-butyne 2a to α-imino ester 1 is not observed when IrCl.2COD, Zn(OTf)$_2$, ZnCl$_2$ or Sc(OTf)$_3$ is used as a catalyst precursor (entry 1 of Table 1). The desired product 3a is obtained with good yields when catalyst precursors CuPF$_6$.4MeCN (entry 3) and CuOTf.0.5C$_6$H$_6$ are used (entry 4). Some other copper complexes, e.g., including Cu(OTf)$_2$ (entry 5), CuCl, CuBr (entry 2), CuO$_2$ and CuOAc (entry 1) show lower or relatively undetectable catalytic activity.

EXAMPLE 2

Effect of the Inclusion of an Amine Base

TABLE 2

Asymmetric addition of 4-phenyl-1-butyne to α-imino ester

| Entry | Catalyst | Additive | Yield* (%) | Ee (%) |
|---|---|---|---|---|
| 1 | CuPF$_6$•4MeCN/4 | — | trace | nd. |
| 2 | CuPF$_6$•4MeCN/5 | — | 92 | <5 |
| 3 | CuPF$_6$•4MeCN/6 | — | trace | nd. |
| 4 | CuPF$_6$•4MeCN/7 | — | 75 | <5 |
| 5 | CuPF$_6$•4MeCN/8a | — | 73 | 59 |
| 6 | CuPF$_6$•4MeCN/8a | A | trace | nd. |
| 7 | CuPF$_6$•4MeCN/8a | B | trace | nd. |
| 8 | CuPF$_6$•4MeCN/8a | C | 86 | 57 |
| 9 | CuPF$_6$•4MeCN/8a | D | 90 | 57 |
| 10 | CuPF$_6$•4MeCN/8b | D | 93 | 69 |
| 11 | CuPF$_6$•4MeCN/9 | D | 91 | 77 |
| 12 | CuOTf•0.5C$_6$H$_6$/9 | D | 91 | 82 |
| 13[†] | CuOTf•0.5C$_6$H$_6$/9 | D | 90 | 85 |
| 14 | Cu(OTf)$_2$/9 | D | 78 | 56 |

Condition:

1 (0.25 mmol) and 2a (0.5 mmol) in CH$_2$Cl$_2$ (1.5 mL) at 0° C.

A: 0.5 eq. Et$_3$N,

B: 0.5 eq. $^i$Pr$_2$NH,

C: 0.5 eq. PMPNH$_2$,

D: 0.1 eq. PMPNH$_2$.

*Isolated yields.

[†]Reaction is conducted at about −10° C.

The addition of amine bases and the use of other copper sources and structurally different Pybox ligands are explored in Table 2, supra. It is known that metal alkynilides employed in C—C bond formation reactions are generated in the presence of an amine base, such as $Et_3N$. Surprisingly, in the alkynylation system of the present invention, the reaction is markedly retarded by adding 0.5 eq $Et_3N$ or $^iPr_2NH$ (entries 6,7). In contrast, the use of 0.5 or 0.1 equivalent PMP—$NH_2$ as additives increase the yields of 3 from 73% to 86% and 90% respectively with no diminution of enantioselectivity (entries 5, 8, 9). Subsequent careful optimization lead to conditions using $CuOTf.0.5C_6H_6$ as a transition metal source and conformationally more restricted Pybox (9) as a chiral ligand at about −10° C. afford the desired product 3 in 90% yield and 85% enantiomeric excess ("ee").

EXAMPLE 3

Alkynylation of α-Imino Esters Catalyzed by CuOTf.0.5C6H6/Pybox (9)

TABLE 3

Alkynylation of α-imino ester catalyzed by $CuOTf•0.5C_6H_6/9$

| Entry | Alkyne | Product | Yield* (%) | Ee (%) |
|---|---|---|---|---|
| 1 | ≡—CH₂CH₂Ph | 3a | 90 | 85 |
| 2 | ≡—CH₂Ph | 3b | 92 | 83 |
| 3 | ≡—(CH₂)₅CH₃ | 3c | 89 | 91 |
| 4 | ≡—cyclopropyl | 3d | 92 | 79 |
| 5 | ≡—CH₂Si(CH₃)₃ | 3e | 63 | 77 |
| 6 | ≡—Si(CH₃)₃ | 3f | 55 | 48 |

*Isolated yields.

The direct alkynylation of α-imino ester 1 using a spectrum of terminal alkynes are performed, and the representative results are summarized in Table 3, supra. In a like manner as in the addition of 4-phenyl-1-butyne (entry 1), the addition reactions of 3-phenyl propyne (entry 2), 1-octyne (entry 3) and cyclopropylacetylene (entry 4) provide the corresponding alkynylation products in good yields and enantiomeric excesses. Whereas, using alkynes with bulky substituted group close to the triple bond, such as trimethylsilyacetylene (entry 6), led to lower reaction rate and enantioselectivity. Noticeably, the present cyclopropylacetylene addition to imino ester 1 (entry 4) represents a new direct and convenient access to α-amino acid derivatives containing conformationally constrained cyclopropane rings.

The following lists the conditions of the analyses of the products in Table 3 of Example 3, i.e., 3a-3f.

Ethyl-2-(p-methoxyphenylamino)-6-phenyl-3-hexynoate. Compound 3a is obtained in 90% yield by using the general procedure. The ee value (85%) is determined by HPLC analysis with a chiral column [Chiralcel AD, 90:10 hexane:i-PrOH, 1.0 mL/min: $t_R$ (major)=11.48 min, $t_R$(minus)=16.75 min]. $[\alpha]_D^{20}$ −64.7° (c 0.5, $CHCl_3$); $^1H$ NMR (500 MHz $CDCl_3$): δ=7.28-7.25 (m, 2H), 7.20-7.16 (m, 3H), 6.80-6.78 (m, 2H), 6.67-6.65 (m, 2H), 4.69 (t, 1H, J=2.3 Hz), 4.27-4,24 (q, 2H, J=7.5 Hz), 3.76 (s, 3H), 2.80-2.77 (t, 2H, J=7.3 Hz), 2.49-2.46 (dt, 2H, J=7.3, 2.0 Hz), 1.31-1.28 (t, 3H, J=7.5 Hz); $^{13}C$ NMR (125 MHz, $CDCl_3$): δ=169.5, 153.7, 140.6, 137.6, 128.7, 128.6, 126.6, 116.5, 114.9, 84.8, 75.4, 62.5, 55.9, 50.5, 34.9, 21.1, 14.3; HRMS (ESI) calc. for $C_{21}H_{24}NO_3$ $[M+1]^+$: 338.1756, found: 338.1782.

Ethyl-2-(p-methoxyphenylamino)-5-phenyl-3-pentynoate. Compound 3b is obtained in 92% yield by using the general procedure. The ee value (83%) is determined by HPLC analysis using a chiral column [Chiralcel AD, 90:10 hexane:i-PrOH, 1.0 mL/min: $t_R$ (minor)=21.49 min, $t_R$ (major)=35.00 min]. $[\alpha]_D^{20}$ −38.1° (c 0.4, $CHCl_3$); $^1H$ NMR (500 MHz, $CDCl_3$): δ=7.31-7.24 (m, 5H), 6.83-6.81 (m, 2H), 6.74-6.72 (m, 2H), 4.83 (t, 1 H, J=2.2 Hz), 4.32-4.28 (q, 2H, J=7.2 Hz), 3.76 (s, 3H), 3.62 (d, 1H, 2.0 Hz), 1.27 (t, 3H, J=7.3 Hz); $^{13}C$ NMR (125 MHz, $CDCl_3$): δ=169.5, 153.6, 139.7, 136.3, 128.7, 128.1, 126.9, 116.4, 115.0, 82.9, 72.8, 62.5, 55.8, 50.5, 25.2, 14.3; HRMS (ESI): Calcd for $C_{20}H_{22}NO_3$ (M++1): 324.1600, found ($M^+$+1): 324.1596.

Ethyl-2-(p-methoxyphenylamino)-3-decynoate. Compound 3c is obtained in 89% yield by using the general procedure. The ee value (91%) is determined by HPLC analysis using a chiral column [Chiralcel AD, 90:10 hexane:i-PrOH, 1.0 mL/min: $t_R$ (major)=9.96 min, $t_R$ (minus)=12.63 min]. $[\alpha]_D^{20}$ −62.3° (c 0.4, $CHCl_3$); $^1H$ NMR (500 MHz, $CDCl_3$): δ=6.79-6.77 (m, 2H), 6.70-6.68 (m, 2H), 4.70 (t, 1H, J=2.3 Hz 1H), 4.29-4.24 (q, 2H, 7.3 Hz), 3.75 (s, 3H), 2.19-2.15 (dt, 2H, J=7.0, 2.3 Hz), 1.47-1.44 (m, 2H), 1.34-1.20 (m, 13H), 0.89-0.86 (t, 3H, J=7.0 Hz); $^{13}C$ NMR (125 MHz, $CDCl_3$): δ=169.6, 153.7, 139.3, 116.6, 114.9, 86.0, 75.0, 62.4, 55.8, 50.6, 31.5, 28.6, 28.5, 22.8, 18.9, 14.3, 14.2; HRMS (ESI) calc. for $C_{19}H_{28}NO_3$ $[M+1]^+$: 318.2069, found: 318.2091.

Ethyl-2-(p-methoxyphenylamino)-4-cyclopropyl-3-butynoate. Compound 3d is obtained in 92% yield by using the general procedure. The ee value (79%) is determined by HPLC analysis using a chiral column [Chiralcel AD, 95:15 hexane:i-PrOH, 1.0 mumin: $t_R$ (major)=11.08 min, $t_R$ (minus)= 19.46 min]. $[\alpha]_D^{20}$ −47.4° (c 0.7, $CHCl_3$); $^1H$ NMR (500 MHz, CDCl$_3$): δ=6.78-6.74 (m, 2H), 6.66-6.62 (m, 2H), 4.64 (d, 1H, J=2.3 Hz), 4.26-4.21 (q, 2H, J=7.0), 3.17 (s, 3H), 1.26 (t, 3H, J=7.0 Hz), 1.12-1.08 (m, 1H), 0.67-0.64 (m, 2H), 0.63-0.60 (m, 2H); $^{13}$C NMR (125 MHz, CDCl$_3$): δ=169.9, 153.7, 140.1, 116.4, 115.2, 88.8, 70.6, 62.6, 56.1, 50.7, 14.5, 8.8, 8.7; HRMS (ESI) calc. for C$_{16}$H$_{20}$NO$_3$ [M+1]$^+$: 274.1443 found: 274.1453.

Ethyl-2-(p-methoxyphenylamino)-5-(trimethylsilyl)-3-pentynoate. Compound 3e is obtained in 63% yield by using the general procedure. The ee value (77%) is determined by HPLC analysis using a chiral column [Chiralcel AD, 90:10 hexane:i-PrOH, 0.7 mL/min: t$_R$ (major)=18.03 min, t$_R$ (minus)=27.63 min]. [α]$_D^{20}$ −36.3° (c 0.5, CHCl$_3$); $^1$H NMR (500 MHz, CDCl$_3$): δ=6.79-6.72 (m, 2H), 6.68-6.66 (m, 2H), 4.71 (t, 1H, 2.5 Hz), 4.28-4.24 (q, 2H, J=7.2 Hz), 3.74 (s, 3H), 1.46-1.45 (d, 2H, J=3.0 Hz), 1.32-1.29 (t, 3H, J=7.3 Hz), 0.04 (s, 9H); δ=169.8, 153.5, 139.6, 116.3, 114.9, 83.7, 73.9, 62.2, 55.9, 50.5, 14.3, 7.3, −1.9; HRMS (ESI) calc. for C$_{17}$H$_{26}$NO$_3$Si [M+1]$^+$: 320.1682, found: 320.1711.

Ethyl-2-(p-methoxyphenylamino)-4-(trimethylsilyl)-3-butynoate. Compound 3f is obtained in 55% yield by using the general procedure. The ee value (48%) is determined by HPLC analysis using a chiral column [Chiralcel AD, 90:10 hexane:i-PrOH, 1.0 mL/min: t$_R$ (major)=6.97 min, t$_R$ (minus)= 9.15 min]. [α]$_D^{20}$ −98.5° (c 0.3, CHCl$_3$); $^1$H NMR (500 MHz, CDCl$_3$): δ=6.65-6.63 (m, 2H), 6.55-6.53 (m, 2H), 4.58 (s, 1H), 4.15-4.11 (q, 2H, J=7.0), 3.60 (s, 3H), 1.15(t, 3H, J=7.0 Hz); $^{13}$C NMR (125 MHz, CDCl$_3$): δ=169.0, 153.6, 139.5, 116.4, 114.9, 100.1, 90.0, 62.5, 55.8, 51.2, 14.2, −0.1; HRMS (ESI) calc. for C$_{16}$H$_{24}$NO$_3$Si [M+1]$^+$: 306.1525, found: 306.1529.

EXAMPLE 4

Utility of Asymmetric Alkynylated α-Imino Esters

The products of the processes of the present invention, i.e., asymmetric alkynylated α-imino esters can be used to synthesize optically active unnatural α-amino acid derivatives. An example of this is shown in Scheme 1, below, which is a modification of the product 3b in Example 3 to yield a bishomophenylalanine derivative, or (R)-12 in Scheme 1, which is a key intermediate of pharmaceutically interesting peptides used in growth hormone products.

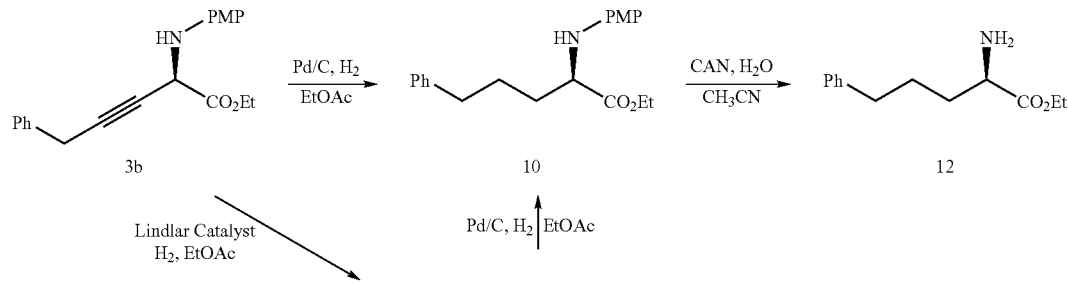

Scheme 1.

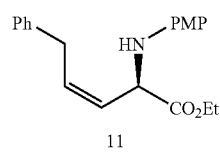

11

The alkynylation product 3b is hydrogenated to 10 in quantitative yield. Subsequent treatment of 10 with cerium ammonium nitrate (CAN) affords the target molecule in a 76% yield. The absolute configuration of 3b is determined to be R by this transformation $\{[\alpha]_D^{20}$ −11.7° (c 0.4, CHCl$_3$) for (R)-12; ref 47, $[\alpha]_D^{20}$ +14.5° (c 0.4, CHCl$_3$) for its S enantiomer}. In addition, semireduction of 3b in the presence of a Lindlar catalyst yields a (Z)-vinyl amino acid derivative 11, a β,γ-vinyl amino acid derivative. The catalytic asymmetric alkynylation of α-imino ester 1, combined with semireduction, provides the first catalytic introduction of vinyl group to amino acid derivatives. The hydrogenation of 11 using Pd/C also furnished intermediate 10 in quantitative yield.

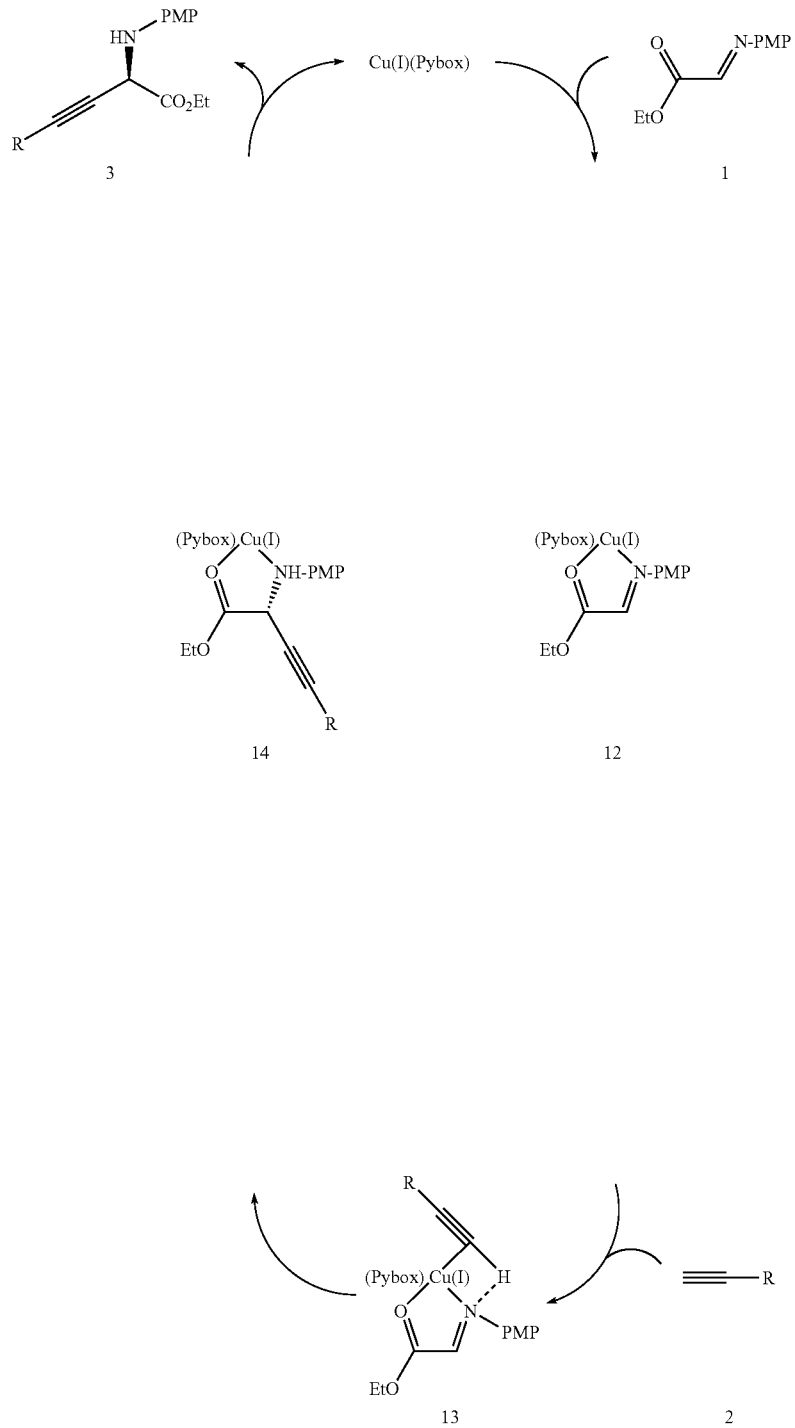

Scheme 2. Proposed mechanism for the alkynylation of α-iminoesters

Without being bound to a particular theory, a speculated mechanism for the catalytic alkynylation of α-imino ester is outlined in Scheme 2. The successive complexation of substrate 1 and alkyne 2 to the catalyst center produces intermediate 13 which undergoes intramolecular alkyne transfer to afford intermediate 14. Subsequent dissociation of product 3 from 14 concomitantly regenerates the catalyst.

Thus, the present invention provides a method for the asymmetric addition of a terminal alkyne to an α-imino ester that results in a good yield and good ee's.

It is understood that while the present invention has been described in conjunction with the detailed description thereof that the foregoing description is intended to illustrate and not limit the scope of the invention, which is defined by the scope of the following claims. Other aspects, advantages and modifications are within the scope of the claims.

What is claimed is:

1. A method for the preparation of asymmetric alkynylated α-amino esters of the formula

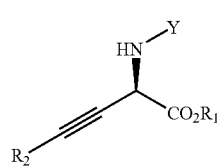

(III)

wherein $R_1$ and $R_2$ are independently optionally substituted alkyl, cycloalkyl, aryl or heteroaryl, and Y is hydrogen or a nitrogen protecting group; which method comprises reacting an α-imino ester of formula

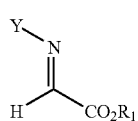

(I)

wherein $R_1$ and Y have meanings as defined for formula III with a terminal alkyne of formula

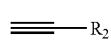

(II)

wherein $R_2$ has meaning as defined for formula III.

2. The method of claim 1, wherein said reacting is in the presence of a catalyst.

3. The method of claim 2, wherein said reacting is in the presence of a catalytic amount of an amine base.

4. The method of claim 2, wherein said amine base is PMP—$N_2$.

5. The method of claim 2, wherein said catalyst comprises a transition metal, a transition metal salt, or a transition metal complex.

6. The method of claim 5, wherein said transition metal complex is selected from the group consisting of $CuPF_5.4MeCN$ and $CuOTf.0.5C_6H_6$.

7. The method of claim 5, wherein said catalyst comprises a chiral ligand.

8. The method of claim 7, wherein said chiral ligand is selected from the group consisting of

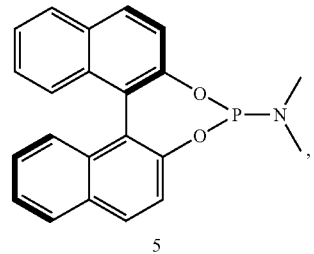

5

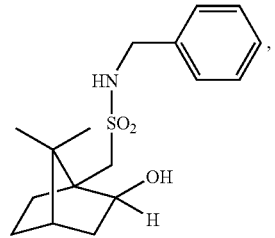

7

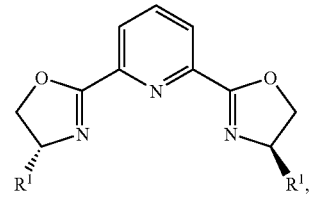

Pybox (8a): $R^1 = {}^iPr$
Pybox (8b): $R^1 = Ph$

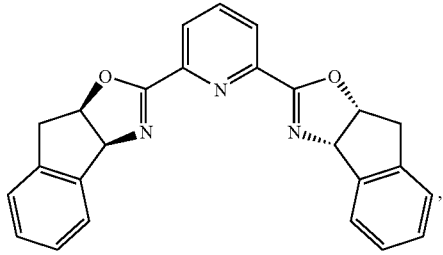

Pybox (9)

enantiomers thereof, and enantiomeric mixtures thereof.

9. The method of claim 1, wherein $R_1$ is alkyl.

* * * * *